US012704495B2

(12) United States Patent
Bokhari et al.

(10) Patent No.: US 12,704,495 B2
(45) Date of Patent: Aug. 11, 2026

(54) EVALUATING BIOLOGICAL MATERIALS AT RESERVOIR CONDITIONS

(71) Applicant: Saudi Arabian Oil Company, Dhahran (SA)

(72) Inventors: Ameerah Mohammed Madani Bokhari, Thuwal (SA); Abdulrahman B. Aljedaani, Thuwal (SA)

(73) Assignee: Saudi Arabian Oil Company, Dhahran (SA)

(*) Notice: Subject to any disclaimer, the term of this patent is extended or adjusted under 35 U.S.C. 154(b) by 331 days.

(21) Appl. No.: 18/607,915

(22) Filed: Mar. 18, 2024

(65) Prior Publication Data

US 2025/0290913 A1 Sep. 18, 2025

(51) Int. Cl.
*G01N 33/24* (2006.01)

(52) U.S. Cl.
CPC .......... *G01N 33/24* (2013.01); *G01N 33/243* (2024.05)

(58) Field of Classification Search
CPC ............................ G01N 33/24; G01N 33/243
See application file for complete search history.

(56) References Cited

U.S. PATENT DOCUMENTS

| | | | |
|---|---|---|---|
| 10,443,363 B2 | 10/2019 | Canalizo-Hernandez et al. | |
| 10,976,296 B2 | 4/2021 | Al-Otaibi et al. | |
| 11,585,741 B2 | 2/2023 | Linnemeyer et al. | |
| 11,608,723 B2 | 3/2023 | Al-Qasim et al. | |
| 2008/0199862 A1* | 8/2008 | Gu | F04B 19/006 435/287.2 |
| 2015/0369718 A1 | 12/2015 | Chertov et al. | |
| 2020/0240972 A1* | 7/2020 | Henderson | G01N 33/241 |
| 2021/0166404 A1* | 6/2021 | Thoroddsen | G01S 17/58 |
| 2023/0321601 A1 | 10/2023 | AlGhunaimi et al. | |
| 2024/0189792 A1 | 6/2024 | Nadhreen et al. | |

FOREIGN PATENT DOCUMENTS

WO WO-2011067559 A1 * 6/2011 ....... G01N 33/48721

OTHER PUBLICATIONS

Broda et al., "Construction and Evaluation of a Bio-Engineered Pump to Enable Subpulmonary Support of the Fontan Circulation: A Proof-of-Concept Study," The Journal of Heart and Lung Transplantation, Apr. 2020, 39(4S):417, 1 page.

Fernandez et al., "Design of a High-Pressure Research Flow Loop for the Experimental Investigation of Liquid Loading in Gas Wells," SPE Projects, Facilities & Construction, Jun. 2010, 5:76-88, 13 pages.

Onyemara et al., "Development of a New High-Pressure High-Temperature Technology for Advanced Screening of Biosurfactants and Injection of Microbes in Porous Rocks during Low-Salinity EOR Processes," presented at the SPE Nigeria Annual International Conference and Exhibition, Lagos, Nigeria, Aug. 5-7, 2019, 26 pages.

Pannekens et al., "Oil reservoirs, an exceptional habitat for microorganisms," New Biotechnology, 2019, 49:1-9, 9 pages.

* cited by examiner

*Primary Examiner* — Francis C Gray
(74) *Attorney, Agent, or Firm* — Fish & Richardson P.C.

(57) ABSTRACT

Systems and methods for evaluating biological materials at reservoir conditions include a reactor housing and a plurality of test columns having source rock sample holders. The plurality of test columns is disposed within the reactor housing. A pump is fluidly coupled to the reactor housing. A heating element is coupled to the reactor housing; and one or more sensors are coupled to the test columns configured to measure properties of biomaterials or biochemical interactions in the rock samples.

20 Claims, 5 Drawing Sheets

EVALUATING BIOLOGICAL MATERIALS AT RESERVOIR CONDITIONS

TECHNICAL FIELD

This disclosure generally relates to evaluating biological materials at reservoir conditions.

BACKGROUND

As part of the global sustainability efforts in the oil and gas industry, nature-based solutions have been gaining momentum during the past decade aiming to reduce the negative environmental impacts of hydrocarbons in many industrial practices. Nature-based solutions can include a wide variety of materials that can be efficient, economic and environmentally friendly. Examples of these materials include biosurfactants, biopolymers, fatty acids, and solvents. Various microbial groups can be utilized for oil and gas operations such as enhanced oil recovery, carbon dioxide ($CO_2$) biomineralization, hydrogen ($H_2$) production and storage, and hydrogen sulfide ($H_2S$) mitigation.

SUMMARY

This disclosure provides an approach to assessing the complex interactions between the biological materials, the reservoir rock, and hydrocarbons in the reservoir produced by using biological material in oil and gas operations. The comprehensive evaluation and real-time monitoring of laboratory scale interactions provided by this approach can offer insight into the reservoir interactions to better achieve a desired outcome.

This disclosure describes systems and methods for evaluating biological materials at reservoir conditions. A laboratory scale system (e.g., an artificial reservoir) can be used to test the functions and/or interactions of biological materials with source rock samples at pressures and temperatures that mimic conditions in a subsurface reservoir. The system can include one or more advanced sensors to measure properties of biological materials in the source rock samples. The system can also include a high-speed camera to observe rapid interactions of the biological materials.

Systems can include a reactor housing where at least a portion of the reactor housing includes a transparent material. A light source can be positioned to emit light through the transparent material of the reactor housing with a high speed camera positioned on an opposite side of the light source to receive light emitted by the light source. Multiple test columns can include source rock sample holders. The test columns can be disposed within the reactor housing between the light source and the high speed camera. A pump can be fluidly coupled to the reactor housing. A heating element can be coupled to the reactor housing, and one or more sensors can be coupled to the test columns. The one or more sensors operable to measure properties of biomaterials or biochemical interactions in rock samples in the test columns.

Implementations of the systems and methods of this disclosure can provide various technical benefits. Biochemical interactions can be investigated in reservoir conditions in real-time. Lab-scale compatibility tests can be performed for new bio-based materials prior to field deployment. For example, compatibility tests can include assessing different reservoir parameters including salinity, temperature, pH, pressure, and fluid dynamics when bio-based materials are applied to reservoir rock. The compatibility tests can determine the ability of the bio-based materials to withstand the reservoir conditions. Based on the compatibility tests, an application specific bio-based material can be selected. Biochemical conditions of bio-based materials can be selected to reduce costs, lower energy consumption, and define better alternatives to petroleum-based materials. Using the systems and methods of this disclosure, sustainable solutions (e.g., bio-based solutions) for upstream oil and gas operations such as enhanced oil and gas production, hydraulic fracturing operations, optimizing drilling fluids, reducing lost circulation, mitigating biogenic $H_2S$, treating corrosion, and enhanced oil recovery can be tested. The systems and methods of this disclosure can aid eliminating toxicity and hazardousness of non-eco-friendly chemicals.

The details of one or more implementations of these systems and methods are set forth in the accompanying drawings and the description below. Other features, objects, and advantages of these systems and methods will be apparent from the description and drawings, and from the claims.

DESCRIPTION OF DRAWINGS

Like reference symbols in the various drawings indicate like elements.

DETAILED DESCRIPTION

This disclosure describes systems and methods for evaluating biological materials at reservoir conditions. A laboratory scale system (e.g., an artificial reservoir) can be used to test the functions and/or interactions of biological materials with source rock samples at pressures and temperatures that mimic conditions in a subsurface reservoir. The system can include one or more advanced sensors to measure properties of biological materials in the source rock samples. The system can also include a high-speed camera to observe rapid interactions of the biological materials.

Systems can include a reactor housing where at least a portion of the reactor housing includes a transparent material. A light source can be positioned to emit light through the transparent material of the reactor housing with a high speed camera positioned on an opposite side of the light source to receive light emitted by the light source. Multiple test columns can include source rock sample holders. The test columns can be disposed within the reactor housing between the light source and the high speed camera. A pump can be fluidly coupled to the reactor housing. A heating element can be coupled to the reactor housing, and one or more sensors can be coupled to the test columns. The one or more sensors operable to measure properties of biomaterials or biochemical interactions in rock samples in the test columns.

Figure 1:
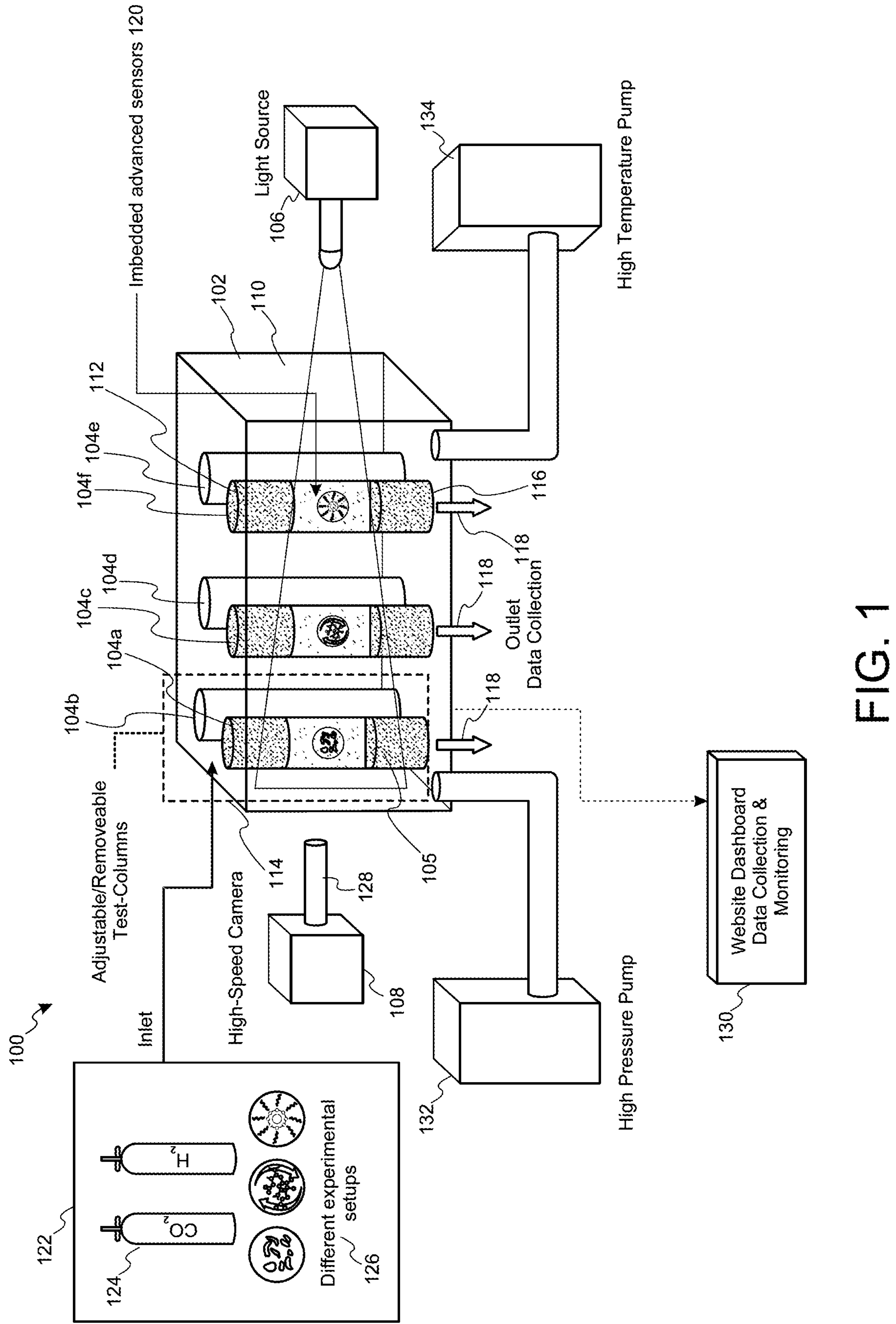
FIG. 1 is a schematic of a system for evaluating biological materials at reservoir conditions.

FIG. 1 is a schematic of a system 100 for evaluating biological materials at reservoir conditions. The system 100 includes a reactor housing 102, test columns 104*a-f* (collectively test columns 104), a light source 106, and a high speed camera 108. At least a portion of the reactor housing includes a transparent material 110. The light source 106 is positioned on one side of the reactor housing and emits light through the transparent material 110 of the reactor housing. The high speed camera 108 is positioned on the opposite side of the reactor housing 102 from the light source 106. The high speed camera receives light from the light source 106 that has propagated through the reactor housing 102 and through the test columns 104.

The test columns 104 are positioned within the reactor housing 102 between the light source 106 and the high speed camera 108. The test columns are made from a transparent material that can withstand reservoir temperatures and pressures. Examples of transparent materials include glass and polymeric materials such as poly methyl methacrylate (PMMA) and polycarbonate. The test columns 104 can be removable from the reactor housing 102. For example, the test columns 104 can be threaded into designated positions within the reactor housing 102. Alternatively, or additionally, the test columns 104 can be attached to the reactor housing 102 using clamps or a clamping mechanism.

The test columns 104 include source rock sample holders to hold samples of source rock 105 (e.g., porous rock, core samples from a subsurface formation). The source rock samples can be injected with biological materials during testing. As shown in FIG. 1, the test columns are isolated from one another. For example, test column 104*a* is not in fluid communication with any of test columns 104*b-f*. Likewise, test column 104*b* is not in fluid communication with any of test columns 104*a* or 104*c-f*, and so on. The isolation of test columns 104 allow multiple experimental scenarios (e.g., different source rock samples, different biological materials, etc.) to be conducted in the reactor housing 102 at the same time. In some implementations, pairs of test columns (e.g., 104*a-b*, 104*c-d*, and 104*e-f*) include the same experimental test conditions for duplication of results.

The test columns 104 included embedded sensors 120 to measure characteristics of the source rock and the biological materials in the test columns 104. In system 100, the embedded sensors can include sensors such as salinity sensors, temperature sensors, pH sensors, bio-materials degradation sensors, and pressure sensors. The embedded sensors can transmit signals to a data processing system 130. The data processing system 130 can record the signals and display tables and/or graphs of the signals on a display device (e.g., a website dashboard). The display device can be updated remotely using a wired or wireless network.

The type of test columns 104 used in the system 100 can depend on the type of test or experimental campaign being conducted. For example, a test processes that captures data through visual recording by the high speed camera 108 uses transparent test columns 104. The examined processes in the test columns 104 can include microbial migration from a first point to a second point within the test column 104; fluid flow when applying bio-based materials such as biosurfactants and biopolymers; microbial interactions with different rock types and fluids; biomineralization of $CO_2$; and thief zone plugging (e.g., plugging of high-permeability zones that divert fluids away from lower permeability target zones). In other examples, non-transparent test columns 104 can be used when the desired data does not need to be visually captured, for example, a test using high pressure, high temperature (HPHT) conditions to determine wettability enhancement, enhanced oil recovery, water-cut reduction, and/or biogenic $H_2S$ production.

At a top end 112 of the test columns 104, the test columns 104 are fluidly coupled to an inlet manifold 114. The inlet manifold 114 is fluidly coupled to experimental inputs 122. The experimental inputs can include gas cylinders 124 (e.g., $CO_2$ or $H_2$) to inject gas into the test columns 104. The experimental inputs can also include various biological materials 126 (e.g., biosurfactants, biopolymers, fatty acids, solvents) that can be injected into the test columns 104 during an experimental campaign.

At a bottom end 116 of the test columns 104, the test columns are coupled to an outlet 118. Fluids and other discharge from the test columns 104 can be collected from the outlets 118 during an experimental campaign. The fluids and other discharge can be tested in a laboratory setting to analyze characteristics of biological materials from the test columns 104. The outlet 118 of each test column 104 is isolated from other outlets 118, and the fluid and other discharge is kept separate for subsequent evaluation.

The high speed camera 108 is equipped with a lens 128 with a magnification sufficient to observe the biological interactions and/or biochemical interactions. For example, the magnification can be 1× or more, 5× or more, 10× or more, 20× or more, 40× or more. The high speed camera 108 is capable of recording video with a resolution of 1 megapixel or more at a rate of at least 1000 frames per second (fps). Lower frame rates (e.g., 50 fps, 100 fps, 500 fps) can be achieved without loss of image resolution, while higher frame rates can be possible at reduced image resolution. The high speed camera 108 is positioned to focus on a desired test columns 104 and the appropriate magnification, focal depth, and working distance of the lens can be selected to obtain focused images of the desired test column 104.

The high speed camera 108 can capture microbial and/or biological material interactions with core samples, other microbial and/or biological material, and fluids within the test columns 104. In some implementations, the microbial and/or biological material interactions take place over hours or days and the high speed camera 108 captures the interactions at one or more times while the interactions take place. For example, the high speed camera 108 can capture a video of the interactions at a repeated interval (e.g., once every 1 minute, once every 10 minutes, once an hour, once every two hours, etc.) throughout the interaction.

The light source 106 has a brightness sufficient to illuminate the high speed video. For example, the light source 106 can be a high-power LED, a halogen light, or a laser. In some implementations, multiple light sources are used to provide sufficient illumination.

A high pressure pump 132 is fluidly coupled to the reactor housing 102. The high pressure pump 132 pressurizes the reactor housing 102 to reservoir pressures (e.g., pressures between 1000 and 2500 psi). The high pressure pump 132 pumps a fluid from a fluid reservoir into the reactor housing 102 to generate pressure. The fluids used in the system 100 can include treated seawater, fresh water, and different types of formation water which contain a wide range of salinities, pH, and impurities such as hydrocarbons. Salinity and electrolyte concentrations can be in the form of ions such as sodium, potassium, and chloride. Salinity ranges can include low salinity (e.g., 0-5 parts per thousand (ppt)), medium salinity (e.g., 5-20 ppt), and high salinity (e.g., 20-50 ppt), depending on the microbial species being used. Industrial waste water with high salinity and with average total dissolved solids (TDS) of 160,000 mg/L can be used. The fluid pH can be, for example, between 5.5 and 7.5, depending on the microbial species and the substrates (e.g., core samples) being used. Table 1 shows an example composition of a fluid that can be used.

TABLE 1

Example fluid composition

| Disposal Water Geochemical Analysis | Range |
|---|---|
| Bicarbonate (ppm) | 100-1500 |
| Carbonate (ppm) | 0 |
| Hydroxide (ppm) | 0 |
| Sulfate (ppm) | 300-4500 |
| Chloride (ppm) | 40,000-105,000 |
| Conductivity (ppm) | more than 10000 |
| Total Iron (ppm) | less than 1 |
| Calcium (ppm) | 13,000-35,000 |
| Magnesium (ppm) | 1500-2500 |
| Sodium (ppm) | 24,000-51,000 |
| Potassium (ppm) | 1900-3000 |
| pH@ 25° C. | 6.3-7.3 |
| TDS (ppm) | 157,000-250,000 |
| Specific Gravity, | 1.1116-1.1202 |
| Barium (ppm) | 5-4 |
| Strontium (ppm) | 50-1300 |
| TSS (ppm) | 150-165 |
| Oil content (ppm) | 10-30,000 |

A heating element 134 (e.g., a high temperature pump) generates heat to elevate the temperature of the reactor housing 102 to reservoir temperatures. For example, the reactor housing 102 can be heated to a temperature between 90° C. and 150° C. A high temperature pump can transport available heat energy from the heating element 134 to the test columns 104, for example, by compressing and expanding refrigerant gases such as hydrofluoro-olefins (HFOs) and natural gas to transport the heat energy. High temperature heat pumps can operate at temperatures higher than 60° C. by using specialized refrigerants, compressors, and thermodynamic system designs.

Example experimental campaigns that can be performed using the system 100 include tests to determine enhanced oil recovery and water-cut reduction, which evaluate the impact of biosurfactants and/or biopolymers to enhance the recovery of trapped oil within the small pores in the source rock samples 105 in the test columns 104. This can be evaluated by the percentage of recovered oil and water-cut before and after the treatment with the bio-materials. Another example test can include assessment of $H_2S$ gas reduction before and after bio-based materials treatment under certain pH and temperatures.

Figure 2:
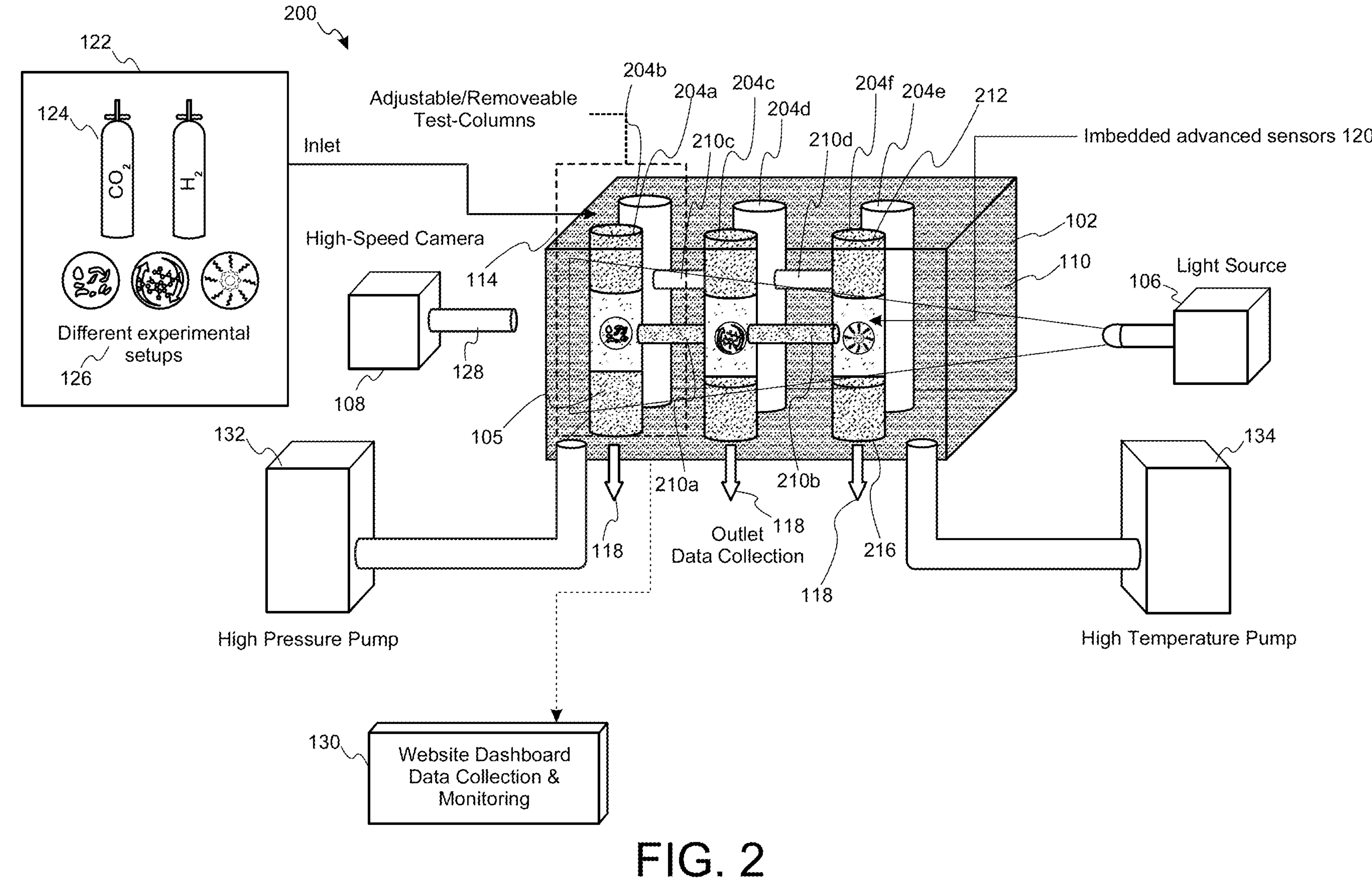
FIG. 2 is a schematic of a system for evaluating biological materials at reservoir conditions including perforated test columns.

FIG. 2 is a schematic of a system 200 for evaluating biological materials at reservoir conditions. System 200 is substantially similar to system 100. However, the system 200 has perforated test columns. This allows the columns to be linked in a series configuration as compared to the parallel configuration in system 100. The system 200 includes perforated test columns 204*a-f*. The perforated test columns 204*a-f* are separated into two or more subsets of test columns. For example, test columns 204*a*, 204*c*, and 204*f* form one subset and test columns 204*b*, 204*d*, and 204*e* form a second subset. The test columns 204 in each subset are fluidly coupled by passageways 210*a-d*. Test column 204*a* is coupled to test column 204*c* by passageway 210*a*. Test column 204*c* is coupled to test column 204*f* by passageway 210*b*. Test column 204*b* is coupled to test column 204*d* by passageway 210*c*. Test column 204*d* is coupled to test column 204*e* by passageway 210*d*.

With the test columns 204 connected in this manner, there is a fluid path from test column 204*a* through the passageway 210*a* to test column 204*c*, and from test column 204*c* through the passageway 210*b* to test column 204*f*. Likewise, there is a fluid path from test column 204*b* through the passageway 210*c* to test column 204*d* and from test column 204*d* through the passageway 210*d* to test column 204*e*.

In some implementations, multiple passageways between test columns 204 within the same subset of test columns can coupled the test columns together. For example, two or more passageways can couple test column 204*a* to test column 204*c*.

Perforated test columns 204 enable observation and measurement of multiple interactions during an experimental campaign. For example, one biological material can be introduced in test column 204*a* while a second, different biological material can be introduced in test column 204*c*, and a third, different biological material can be introduced in test column 204*f*. During the experiment, fluid can flow from test column 204*a* through test column 204*c* to test column 204*f* and vice versa. As the fluid flows between the test columns 204, the different biological materials can be mixed together and interact with one another in different ways than in isolated test columns 104.

The top end 212 of the perforated test columns 204 are coupled to the inlet manifold 114. The bottom ends 216 of the perforated test columns 204 are coupled to the outlets 118.

The perforated test columns 204 are removable from the reactor housing 102. In some implementations, isolated test columns 104 can be removed from the reactor housing and can be replaced with perforated test columns 204.

System 200 is used when the experiment interconnection and sequential interactions between the test columns 204 is desirable. For example, each test column 204 can include different parameters or test conditions (e.g., different rock types, different temperatures, pressures, pH, salinities, etc.), which will result in different reactions and different output when injecting the bio-based materials of interest. Interactions between the test columns 204 can enable an understanding of the bio-based materials' chemical and physical reactions under different conditions, simultaneously.

Alternatively, or additionally, the system 200 can be used to test the bio-based materials' reactions and impact over time from one test column 204 to another test column 204. In such implementations, the test columns 204 can include the same conditions (e.g., same rock types, same temperatures, pressure, pH, salinity, etc.) to better understand the impact of time and the duration of the applied bio-based materials.

System 100 can be used to test different conditions without the need to interconnect the test columns 104. The system 100 can be used to test the dynamics within a single column rather than interconnected test columns 204 in system 200. Example tests that can be performed using system 100 include CO2 mineralization using different types of microbes within a single column and thief zone plugging using bio-based materials such as biomass or biopolymers.

Figure 3A:
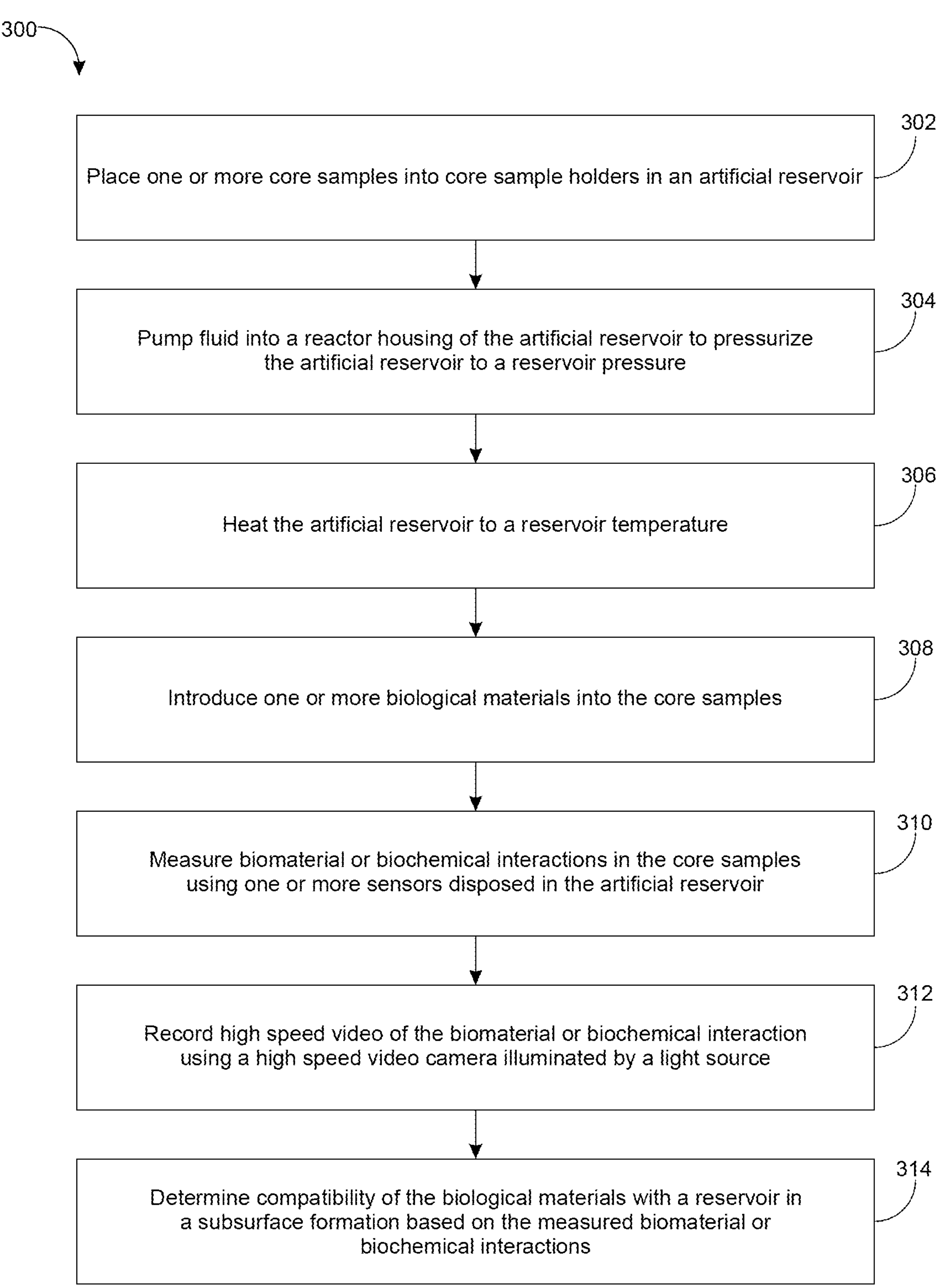
FIG. 3A is a flow chart for a method for evaluating biological materials at reservoir conditions.

FIG. 3A is a flow chart of an example method 300 for evaluating biological materials at reservoir conditions. The method 300 can be performed using an artificial reservoir system (e.g., system 100 or system 200).

One or more core samples are placed into core sample holders in an artificial reservoir (step 302). The core sample holders can be part of test columns including a transparent material The core sample holders can be removable from the artificial reservoir.

A fluid is pumped into a reactor housing of the artificial reservoir to pressurize the artificial reservoir to a reservoir pressure (step 304). For example, the artificial reservoir is pressurized to a pressure in the range 1000-2500 psi.

The artificial reservoir is heated to a reservoir temperature (step 306). For example, the artificial reservoir is heated to a temperature in the range of 90° C. to 160° C. The artificial reservoir can be heated by controlling a heating element to generate heat. The temperature of the artificial reservoir can be maintained at the reservoir temperature by controlling the heating element.

One or more biological materials (e.g., biosurfactants, biopolymers, organic acids, biocides, solvents) is introduced into the core samples (step 308). For example, the biological materials can be introduced by injecting the biological materials through an inlet manifold of the artificial reservoir and into the core samples. In some implementations, measuring biomaterial or biochemical interactions includes determining changes in microbial species in response to nutrients, oilfield chemicals, carbon dioxide, or hydrogen comprised in the core sample.

Biomaterial or biochemical interactions are measured in the core samples using one or more sensors disposed in the artificial reservoir (step 310). Measuring biomaterial or biochemical interactions can include determining changes in microbial species in response to changes in salinity, temperature, pH, or pressure in the artificial reservoir.

High speed video of the biomaterial or biochemical interaction is recorded using a high speed video camera illuminated by a light source (step 312). Images from the high speed video can be processed to extract image data representing dynamic biomaterial and biochemical interactions. For example, data extracted from the image can include physical properties of microbial/biological activities, microbial physical interactions, and flow behavior with different additives.

Compatibility of the biological materials with a reservoir in a subsurface formation is determined based on the measured biomaterial or biochemical interactions (step 314). The compatibility of biological materials with the oil and gas reservoirs can be determined based on the stability of the materials over time without causing damages such as core sample damage, unfavorable clogging of pores in the core samples, generation of $H_2S$ gas, or degradation of oil. Tracking parameters such as oil production/enhancement rates, water cut reduction, and changes in reservoir pressure during the experiments, as well as phase behavior studies, interfacial tension measurements, and rheological evaluations can be used to understand the interaction dynamics. Compatibility of the biological materials can be determined based on the overall performance of the biological materials under different reservoir conditions without negatively impacting the reservoir favorable characteristics.

In some implementations, fluids are collected from the artificial reservoir through an outlet of the core sample holders. Determining compatibility of the biological materials with the reservoir can be based on the measured biomaterial or biochemical interactions and the collected fluids.

In some implementations, such as implementations with perforated test columns, a continuous flow of fluids and/or biological materials can be provided to the test columns for the duration of the test.

In some implementations, such as implementations with non-perforated test columns, a batch of fluid and/or biological material can be provided for each test column for the test, and a continuous flow of fluids does not need to be provided.

Figure 3B:
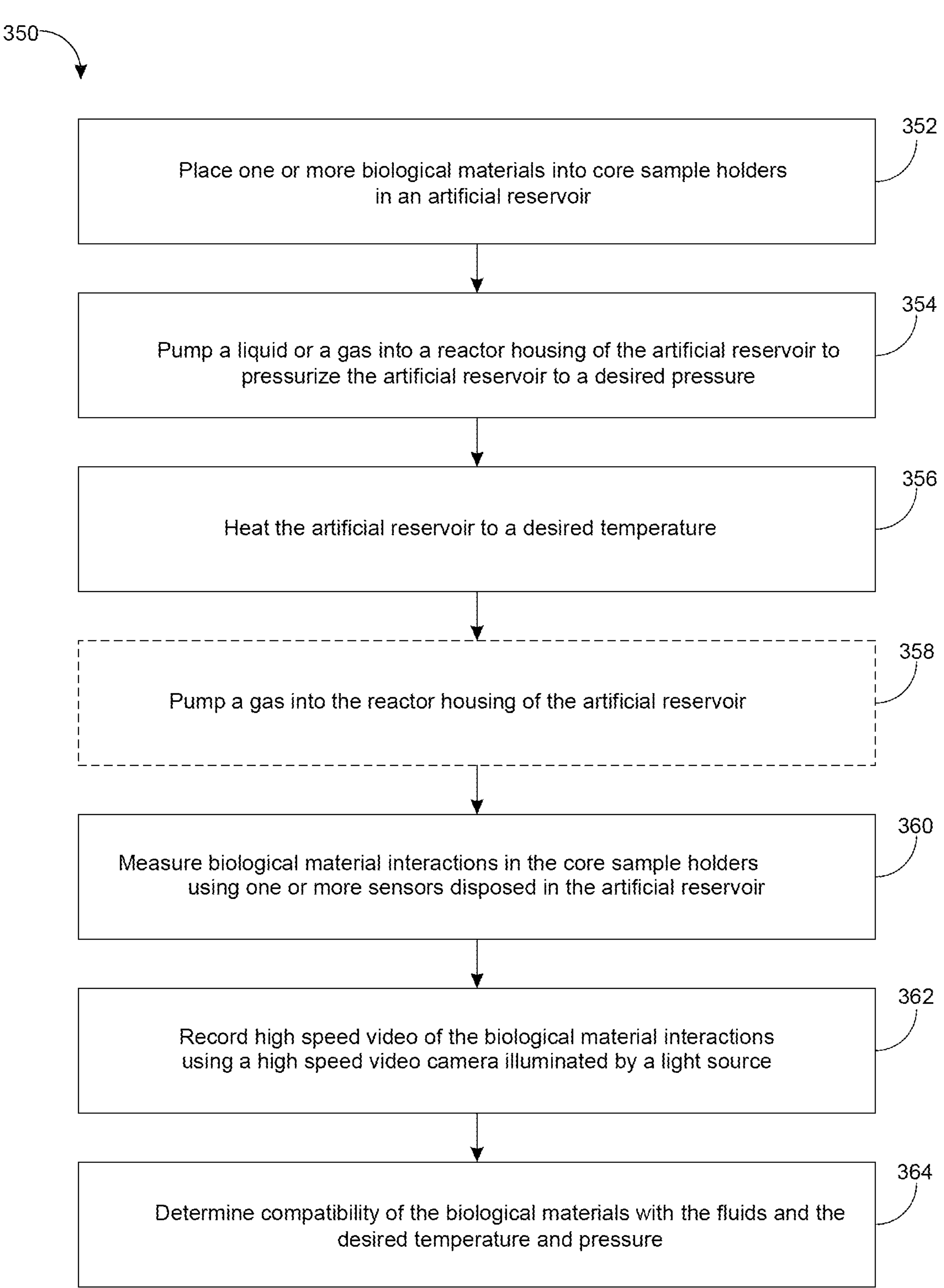
FIG. 3B is a flow chart for a method for evaluating biological materials.

FIG. 3B is a flow chart for another example method 350 for evaluating biological materials using a system such as an artificial reservoir (e.g., system 100 or system 200). One or more biological materials are placed into core sample holders of an artificial reservoir (step 352). A liquid or a gas are pumped into a reactor housing of the artificial reservoir to pressurize the artificial reservoir to a desired pressure (step 354). For example, the artificial reservoir can be pressurized to a pressure of 50 psi or more, 100 psi or more, 500 psi or more, 1000 psi or more, or 2500 psi or less. The artificial reservoir is heated to a desired temperature (step 356). For example, the artificial reservoir can be heated to a temperature of 40° C. or more, 50° C. or more, 100° C. or more, or 200° C. or less. In some implementations, a gas is pumped into the reactor housing of the artificial reservoir (step 358). For example, the gas can be pumped into the reactor housing to interact with the biological materials.

Biological material interactions in the core sample holders are measured using one or more sensors positioned in the artificial reservoir (step 360). For example, the one or more sensors can include a salinity sensor, a temperature sensor, a pH sensor, a bio-materials degradation sensor, and a pressure sensor. Biological material interactions can be measured by measuring changes in the quantities measured by the one or more sensors.

High speed video (e.g., 100 fps or more, 500 fps or more, 1000 fps or more) of the biological material interactions is recorded using a high speed video camera illuminated by a light source (step 362). The light source can emit light with wavelengths in the visible spectrum (e.g., 400-700 nanometers (nm)) and/or the near-infrared spectrum (700-2500 nm).

Compatibility of the biological materials with the fluids in the artificial reservoir and the desired temperature and pressure are determined (step 364). For example, compatibility is determined based on the measured biological interactions and the recorded high speed video. A biological material can be determined to be compatible with the fluids and the desired temperature and pressure based on, for example, the stability of the biological materials over time without being damaged.

Figure 4:
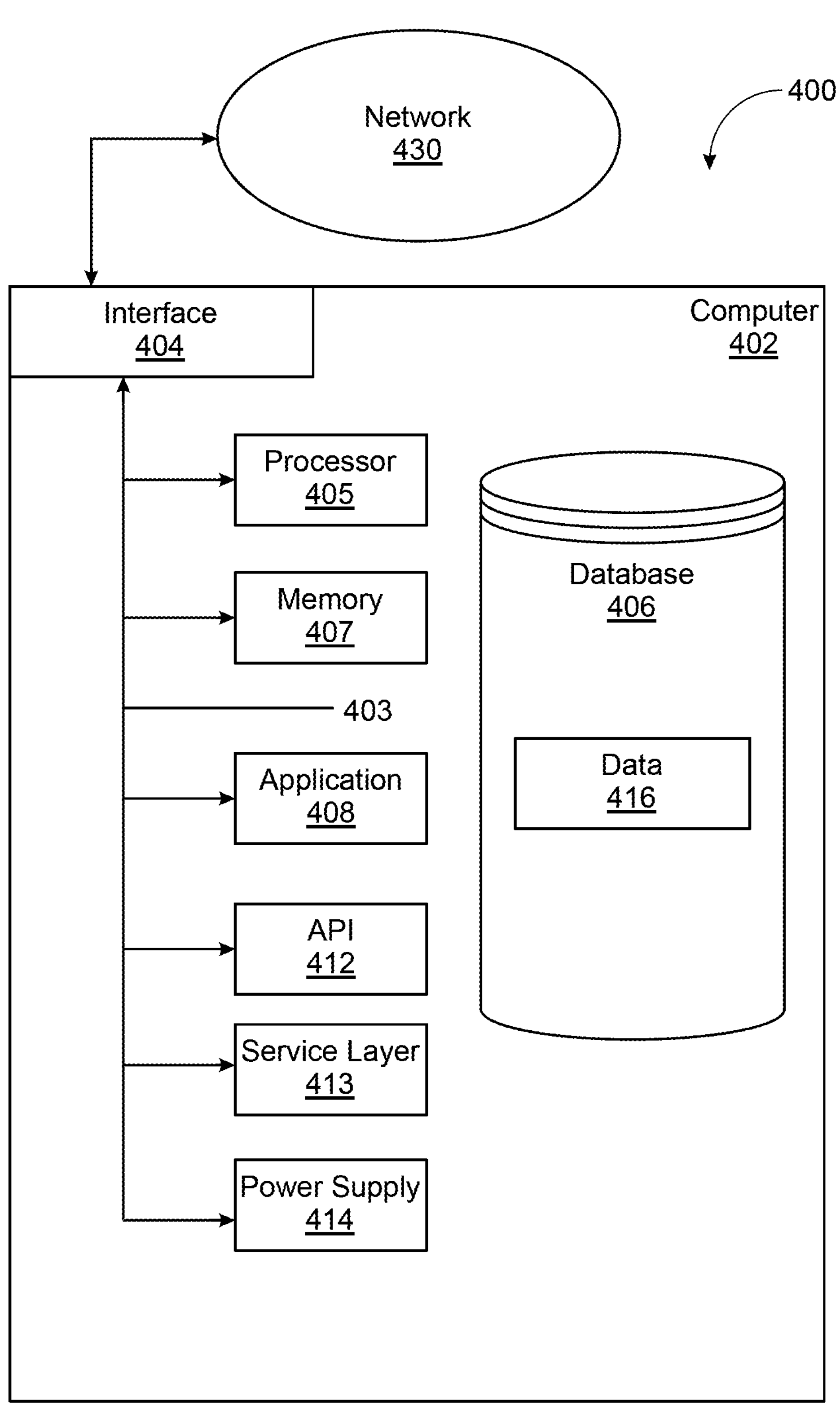
FIG. 4 is a block diagram illustrating an example computer system used to provide computational functionalities associated with described algorithms, methods, functions, processes, flows, and procedures according to some implementations of the present disclosure.

FIG. 4 is a block diagram of an example computer system 400 used to provide computational functionalities associated with described algorithms, methods, functions, processes, flows, and procedures described in the present disclosure, according to some implementations of the present disclosure. The illustrated computer 402 is intended to encompass any computing device such as a server, a desktop computer, a laptop/notebook computer, a wireless data port, a smart phone, a personal data assistant (PDA), a tablet computing device, or one or more processors within these devices, including physical instances, virtual instances, or both. The computer 402 can include input devices such as keypads, keyboards, and touch screens that can accept user information. Also, the computer 402 can include output devices that can convey information associated with the operation of the computer 402. The information can include digital data, visual data, audio information, or a combination of information. The information can be presented in a graphical user interface (UI) (or GUI).

The computer 402 can serve in a role as a client, a network component, a server, a database, a persistency, or components of a computer system for performing the subject matter described in the present disclosure. The illustrated computer 402 is communicably coupled with a network 430. In some implementations, one or more components of the computer 402 can be configured to operate within different environments, including cloud-computing-based environments, local environments, global environments, and combinations of environments.

At a high level, the computer 402 is an electronic computing device operable to receive, transmit, process, store, and manage data and information associated with the described subject matter. According to some implementations, the computer 402 can also include, or be communicably coupled with, an application server, an email server, a web server, a caching server, a streaming data server, or a combination of servers.

The computer 402 can receive requests over network 430 from a client application (for example, executing on another computer 402). The computer 402 can respond to the received requests by processing the received requests using software applications. Requests can also be sent to the computer 402 from internal users (for example, from a command console), external (or third) parties, automated applications, entities, individuals, systems, and computers.

Each of the components of the computer 402 can communicate using a system bus 403. In some implementations, any or all of the components of the computer 402, including hardware or software components, can interface with each other or the interface 404 (or a combination of both), over the system bus 403. Interfaces can use an application programming interface (API) 412, a service layer 413, or a combination of the API 412 and service layer 413. The API 412 can include specifications for routines, data structures, and object classes. The API 412 can be either computer-language independent or dependent. The API 412 can refer to a complete interface, a single function, or a set of APIs.

The service layer 413 can provide software services to the computer 402 and other components (whether illustrated or not) that are communicably coupled to the computer 402. The functionality of the computer 402 can be accessible for all service consumers using this service layer. Software services, such as those provided by the service layer 413, can provide reusable, defined functionalities through a defined interface. For example, the interface can be software written in JAVA, C++, or a language providing data in extensible markup language (XML) format. While illustrated as an integrated component of the computer 402, in alternative implementations, the API 412 or the service layer 413 can be stand-alone components in relation to other components of the computer 402 and other components communicably coupled to the computer 402. Moreover, any or all parts of the API 412 or the service layer 413 can be implemented as child or sub-modules of another software module, enterprise application, or hardware module without departing from the scope of the present disclosure.

The computer 402 includes an interface 404. Although illustrated as a single interface 404 in FIG. 4, two or more interfaces 404 can be used according to particular needs, desires, or particular implementations of the computer 402 and the described functionality. The interface 404 can be used by the computer 402 for communicating with other systems that are connected to the network 430 (whether illustrated or not) in a distributed environment. Generally, the interface 404 can include, or be implemented using, logic encoded in software or hardware (or a combination of software and hardware) operable to communicate with the network 430. More specifically, the interface 404 can include software supporting one or more communication protocols associated with communications. As such, the network 430 or the interface's hardware can be operable to communicate physical signals within and outside of the illustrated computer 402.

The computer 402 includes a processor 405. Although illustrated as a single processor 405 in FIG. 4, two or more processors 405 can be used according to particular needs, desires, or particular implementations of the computer 402 and the described functionality. Generally, the processor 405 can execute instructions and can manipulate data to perform the operations of the computer 402, including operations using algorithms, methods, functions, processes, flows, and procedures as described in the present disclosure.

The computer 402 also includes a database 406 that can hold data for the computer 402 and other components connected to the network 430 (whether illustrated or not). For example, database 406 can hold data 416 (e.g., resistivity data). For example, database 406 can be an in-memory, conventional, or a database storing data consistent with the present disclosure. In some implementations, database 406 can be a combination of two or more different database types (for example, hybrid in-memory and conventional databases) according to particular needs, desires, or particular implementations of the computer 402 and the described functionality. Although illustrated as a single database 406 in FIG. 4, two or more databases (of the same, different, or combination of types) can be used according to particular needs, desires, or particular implementations of the computer 402 and the described functionality. While database 406 is illustrated as an internal component of the computer 402, in alternative implementations, database 406 can be external to the computer 402.

The computer 402 also includes a memory 407 that can hold data for the computer 402 or a combination of components connected to the network 430 (whether illustrated or not). Memory 407 can store any data consistent with the present disclosure. In some implementations, memory 407 can be a combination of two or more different types of memory (for example, a combination of semiconductor and magnetic storage) according to particular needs, desires, or particular implementations of the computer 402 and the described functionality. Although illustrated as a single memory 407 in FIG. 4, two or more memories 407 (of the same, different, or combination of types) can be used according to particular needs, desires, or particular implementations of the computer 402 and the described functionality. While memory 407 is illustrated as an internal component of the computer 402, in alternative implementations, memory 407 can be external to the computer 402.

The application 408 can be an algorithmic software engine providing functionality according to particular needs, desires, or particular implementations of the computer 402 and the described functionality. For example, application 408 can serve as one or more components, modules, or applications. Further, although illustrated as a single application 408, the application 408 can be implemented as multiple applications 408 on the computer 402. In addition, although illustrated as internal to the computer 402, in alternative implementations, the application 408 can be external to the computer 402.

The computer 402 can also include a power supply 414. The power supply 414 can include a rechargeable or non-rechargeable battery that can be configured to be either user- or non-user-replaceable. In some implementations, the power supply 414 can include power-conversion and management circuits, including recharging, standby, and power management functionalities. In some implementations, the power-supply 414 can include a power plug to allow the computer 402 to be plugged into a wall socket or a power source to, for example, power the computer 402 or recharge a rechargeable battery.

There can be any number of computers 402 associated with, or external to, a computer system containing computer 402, with each computer 402 communicating over network 430. Further, the terms "client," "user," and other appropriate terminology can be used interchangeably, as appropriate, without departing from the scope of the present disclosure. Moreover, the present disclosure contemplates that many users can use one computer 402 and one user can use multiple computers 402.

Implementations of the subject matter and the functional operations described in this specification can be implemented in digital electronic circuitry, in tangibly embodied computer software or firmware, in computer hardware, including the structures disclosed in this specification and their structural equivalents, or in combinations of one or more of them. Software implementations of the described subject matter can be implemented as one or more computer programs. Each computer program can include one or more modules of computer program instructions encoded on a tangible, non transitory, computer-readable computer-storage medium for execution by, or to control the operation of, data processing apparatus. Alternatively, or additionally, the program instructions can be encoded in/on an artificially generated propagated signal. The example, the signal can be a machine-generated electrical, optical, or electromagnetic signal that is generated to encode information for transmission to suitable receiver apparatus for execution by a data processing apparatus. The computer-storage medium can be a machine-readable storage device, a machine-readable storage substrate, a random or serial access memory device, or a combination of computer-storage mediums.

The terms "data processing apparatus," "computer," and "electronic computer device" (or equivalent as understood by one of ordinary skill in the art) refer to data processing hardware. For example, a data processing apparatus can encompass all kinds of apparatus, devices, and machines for processing data, including by way of example, a programmable processor, a computer, or multiple processors or computers. The apparatus can also include special purpose logic circuitry including, for example, a central processing unit (CPU), a field programmable gate array (FPGA), or an application specific integrated circuit (ASIC). In some implementations, the data processing apparatus or special purpose logic circuitry (or a combination of the data processing apparatus or special purpose logic circuitry) can be hardware- or software-based (or a combination of both hardware- and software-based). The apparatus can optionally include code that creates an execution environment for computer programs, for example, code that constitutes processor firmware, a protocol stack, a database management system, an operating system, or a combination of execution environments. The present disclosure contemplates the use of data processing apparatuses with or without conventional operating systems, for example LINUX, UNIX, WINDOWS, MAC OS, ANDROID, or IOS.

The methods, processes, or logic flows described in this specification can be performed by one or more programmable computers executing one or more computer programs to perform functions by operating on input data and generating output. The methods, processes, or logic flows can also be performed by, and apparatus can also be implemented as, special purpose logic circuitry, for example, a CPU, an FPGA, or an ASIC.

Computer readable media (transitory or non-transitory, as appropriate) suitable for storing computer program instructions and data can include all forms of permanent/non-permanent and volatile/non-volatile memory, media, and memory devices. Computer readable media can include, for example, semiconductor memory devices such as random access memory (RAM), read only memory (ROM), phase change memory (PRAM), static random access memory (SRAM), dynamic random access memory (DRAM), erasable programmable read-only memory (EPROM), electrically erasable programmable read-only memory (EEPROM), and flash memory devices. Computer readable media can also include, for example, magnetic devices such as tape, cartridges, cassettes, and internal/removable disks.

While this specification contains many specific implementation details, these should not be construed as limitations on the scope of what may be claimed, but rather as descriptions of features that may be specific to particular implementations. Certain features that are described in this specification in the context of separate implementations can also be implemented, in combination, in a single implementation. Conversely, various features that are described in the context of a single implementation can also be implemented in multiple implementations, separately, or in any suitable sub-combination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results. In certain circumstances, multitasking or parallel processing (or a combination of multitasking and parallel processing) may be advantageous and performed as deemed appropriate.

Moreover, the separation or integration of various system modules and components in the previously described implementations should not be understood as requiring such separation or integration in all implementations, and it should be understood that the described program components and systems can generally be integrated together in a single software product or packaged into multiple software products.

Accordingly, the previously described example implementations do not define or constrain the present disclosure. Other changes, substitutions, and alterations are also possible without departing from the spirit and scope of the present disclosure.

Furthermore, any claimed implementation is considered to be applicable to at least a computer-implemented method; a non-transitory, computer-readable medium storing computer-readable instructions to perform the computer-implemented method; and a computer system comprising a computer memory interoperably coupled with a hardware processor configured to perform the computer-implemented method or the instructions stored on the non-transitory, computer-readable medium.

A number of implementations of these systems and methods have been described. Nevertheless, it will be understood that various modifications may be made without departing from the spirit and scope of this disclosure. Accordingly, other implementations are within the scope of the following claims.

Examples

In an example implementation, an artificial reservoir for evaluating biological materials at reservoir conditions includes a reactor housing, at least a portion of the reactor housing includes a transparent material; a light source positioned to emit light through the transparent material of the reactor housing; a high-speed camera positioned on an opposite side of the reactor housing from the light source to receive light emitted by the light source, a plurality of test columns having source rock sample holders, the plurality of test columns disposed within the reactor housing between the light source and the high-speed camera; a pump fluidly coupled to the reactor housing; a heating element coupled to the reactor housing; and one or more sensors coupled to the test columns configured to measure properties of biomaterials or biochemical interactions in the rock samples.

In an aspect combinable with the example implementation, the transparent material includes glass.

In another aspect combinable with any of the previous aspects, the test columns are removably coupled to an interior of the reactor housing.

In another aspect combinable with any of the previous aspects, each of the plurality of test columns includes an outlet at a base of the test column configured to discharge fluids from the rock samples.

In another aspect combinable with any of the previous aspects, two or more of the plurality of test columns are fluidly coupled by conduits extending between a first test column of the plurality and a second test column of the plurality.

Another aspect combinable with any of the previous aspects includes an inlet manifold including an inlet and a plurality of outlets coupled to the plurality of test columns.

In another aspect combinable with any of the previous aspects, the one or more sensors include one or more of a salinity sensor, a temperature sensor, a pH sensor, a biomaterials degradation sensor, and a pressure sensor.

In another example implementation, a method for evaluating biological materials at reservoir conditions includes placing one or more core samples into core sample holders in an artificial reservoir; pumping fluid into a reactor housing to pressurize the artificial reservoir to a reservoir pressure; heating the artificial reservoir to a reservoir temperature; introducing one or more biological materials into the one or more core samples of the artificial reservoir; measuring biomaterial or biochemical interactions in the core samples using one or more sensors disposed in the artificial reservoir; recording high speed video of the biomaterial or biochemical interaction using a high speed video camera illuminated by a light source; and determining compatibility of the biological materials with a reservoir in a subsurface formation based on the measured biomaterial or biochemical interactions.

An aspect combinable with the example implementation includes processing images from the high speed video to extract image data representing dynamic biomaterial and biochemical interactions.

In another aspect combinable with any of the previous aspects, the core sample holders include transparent materials.

In another aspect combinable with any of the previous aspects, measuring biomaterial or biochemical interactions includes determining changes in microbial species in response to changes in salinity, temperature, pH, or pressure in the artificial reservoir.

In another aspect combinable with any of the previous aspects, determining compatibility of the biological materials includes determining a stability of the biological materials over time without causing damages to the one or more core samples.

In another aspect combinable with any of the previous aspects, the biological materials include one or more of bio-surfactants, bio-polymers, organic acids, and biocides.

In another aspect combinable with any of the previous aspects, measuring biomaterial or biochemical interactions includes determining changes in microbial species in response to nutrients, oilfield chemicals, carbon dioxide, or hydrogen comprised in the core sample.

Another aspect combinable with any of the previous aspects includes collecting fluids discharged through an outlet of the core sample holder.

In another aspect combinable with any of the previous aspects, determining compatibility of the biological materials with the reservoir is based on the measured biomaterial or biochemical interactions and the collected fluids.

In another example implementation, an artificial reservoir for evaluating biological materials at reservoir conditions includes a reactor housing; a plurality of test columns having source rock sample holders the plurality of test columns disposed within the reactor housing; a pump fluidly coupled to the reactor housing; a heating element coupled to the reactor housing; and one or more sensors coupled to the test columns configured to measure properties of biomaterials or biochemical interactions in the rock samples.

In an aspect combinable with the example implementation, the one or more sensors include one or more of a salinity sensor, a temperature sensor, a pH sensor, a biomaterials degradation sensor, and a pressure sensor.

Another aspect combinable with any of the previous aspects includes a high-speed camera for visualizing fluid flow in the test columns; and a light source for illuminating the test columns, wherein at least a portion of the reactor housing and the test columns comprise glass through which the high speed camera is configured to observe the source rock samples.

In another aspect combinable with any of the previous aspects, each of the plurality of test columns includes an outlet at a base of the test column configured to discharge fluids from the rock samples.

What is claimed is:

1. An artificial reservoir for evaluating biological materials at reservoir conditions, the artificial reservoir comprising:

- a reactor housing, at least a portion of the reactor housing comprising a transparent material;
- a light source positioned to emit light through the transparent material of the reactor housing;
- a high-speed camera positioned on an opposite side of the reactor housing from the light source to receive light emitted by the light source,
- a plurality of test columns having source rock sample holders, the plurality of test columns disposed within the reactor housing between the light source and the high-speed camera;
- a pump fluidly coupled to the reactor housing;
- a heating element coupled to the reactor housing; and
- one or more sensors coupled to the test columns configured to measure properties of biomaterials or biochemical interactions in the rock samples.

2. The artificial reservoir of claim 1, wherein the transparent material comprises glass.

3. The artificial reservoir of claim 1, wherein the test columns are removably coupled to an interior of the reactor housing.

4. The artificial reservoir of claim 1, wherein each of the plurality of test columns comprises an outlet at a base of the test column configured to discharge fluids from the rock samples.

5. The artificial reservoir of claim 1, wherein two or more of the plurality of test columns are fluidly coupled by conduits extending between a first test column of the plurality and a second test column of the plurality.

6. The artificial reservoir of claim 1, further comprising an inlet manifold comprising an inlet and a plurality of outlets coupled to the plurality of test columns.

7. The artificial reservoir of claim 1 wherein the one or more sensors comprise one or more of a salinity sensor, a temperature sensor, a pH sensor, a bio-materials degradation sensor, and a pressure sensor.

8. A method for evaluating biological materials at reservoir conditions, the method comprising:
- placing one or more core samples into core sample holders in an artificial reservoir;
- pumping fluid into a reactor housing to pressurize the artificial reservoir to a reservoir pressure;
- heating the artificial reservoir to a reservoir temperature;
- introducing one or more biological materials into the one or more core samples of the artificial reservoir;
- measuring biomaterial or biochemical interactions in the core samples using one or more sensors disposed in the artificial reservoir;
- recording high speed video of the biomaterial or biochemical interaction using a high speed video camera illuminated by a light source; and
- determining compatibility of the biological materials with a reservoir in a subsurface formation based on the measured biomaterial or biochemical interactions.

9. The method of claim 8, further comprising: processing images from the high speed video to extract image data representing dynamic biomaterial and biochemical interactions.

10. The method of claim 8, wherein the core sample holders comprise transparent materials.

11. The method of claim 8, wherein measuring biomaterial or biochemical interactions comprises determining changes in microbial species in response to changes in salinity, temperature, pH, or pressure in the artificial reservoir.

12. The method of claim 8, wherein determining compatibility of the biological materials comprises determining a stability of the biological materials over time without causing damages to the one or more core samples.

13. The method of claim 8, wherein the biological materials comprise one or more of bio-surfactants, bio-polymers, organic acids, and biocides.

14. The method of claim 8, wherein measuring biomaterial or biochemical interactions comprises determining changes in microbial species in response to nutrients, oilfield chemicals, carbon dioxide, or hydrogen comprised in the core sample.

15. The method of claim 8, further comprising: collecting fluids discharged through an outlet of the core sample holder.

16. The method of claim 15, wherein determining compatibility of the biological materials with the reservoir is based on the measured biomaterial or biochemical interactions and the collected fluids.

17. An artificial reservoir for evaluating biological materials at reservoir conditions, the artificial reservoir comprising:
- a reactor housing;
- a plurality of test columns having source rock sample holders the plurality of test columns disposed within the reactor housing;
- a pump fluidly coupled to the reactor housing;
- a heating element coupled to the reactor housing; and
- one or more sensors coupled to the test columns configured to measure properties of biomaterials or biochemical interactions in the rock samples.

18. The artificial reservoir of claim 17, wherein the one or more sensors comprise one or more of a salinity sensor, a temperature sensor, a pH sensor, a bio-materials degradation sensor, and a pressure sensor.

19. The artificial reservoir of claim 18, further comprising: a high-speed camera for visualizing fluid flow in the test columns; and a light source for illuminating the test columns, wherein at least a portion of the reactor housing and the test columns comprise glass through which the high speed camera is configured to observe the source rock samples.

20. The artificial reservoir of claim 17, wherein each of the plurality of test columns comprises an outlet at a base of the test column configured to discharge fluids from the rock samples.

* * * * *